(12) United States Patent
Passarelli, Jr.

(10) Patent No.: US 6,951,133 B2
(45) Date of Patent: *Oct. 4, 2005

(54) ELECTROMAGNETIC ACOUSTIC TRANSDUCER WITH RECESSED COILS

(76) Inventor: Frank Passarelli, Jr., 4634 Tam O Shanter Dr., Westlake Village, CA (US) 91362

(*) Notice: Subject to any disclaimer, the term of this patent is extended or adjusted under 35 U.S.C. 154(b) by 0 days.

This patent is subject to a terminal disclaimer.

(21) Appl. No.: 10/437,363

(22) Filed: May 12, 2003

(65) Prior Publication Data

US 2003/0205088 A1 Nov. 6, 2003

Related U.S. Application Data

(63) Continuation-in-part of application No. 09/991,147, filed on Nov. 13, 2001, now Pat. No. 6,561,035, application No. 10/437,363, and a continuation-in-part of application No. 10/374,372, filed on Feb. 25, 2003, now abandoned.

(60) Provisional application No. 60/360,095, filed on Feb. 25, 2002, and provisional application No. 60/248,991, filed on Nov. 15, 2000.

(51) Int. Cl.[7] ........................ G01N 29/24; G01N 29/06; G01N 29/26

(52) U.S. Cl. ......................... 73/643; 73/622

(58) Field of Search ....................... 73/579, 597, 598, 73/599, 600, 622, 623, 640, 641, 643

(56) References Cited

U.S. PATENT DOCUMENTS

| 4,002,967 | A | * | 1/1977 | Fennell ....................... 324/238 |
| 4,127,035 | A | | 11/1978 | Vasile |
| 4,232,557 | A | | 11/1980 | Vasile |
| 4,471,658 | A | | 9/1984 | Morimoto |
| 4,976,148 | A | | 12/1990 | Migliori et al. |
| 5,062,296 | A | | 11/1991 | Migliori |
| 5,456,113 | A | | 10/1995 | Kwun et al. |
| 5,581,037 | A | | 12/1996 | Kwun et al. |
| 5,808,202 | A | | 9/1998 | Passarelli, Jr. |
| 5,895,856 | A | | 4/1999 | Johnson et al. |
| 6,109,108 | A | | 8/2000 | Ohtani et al. |
| 6,119,522 | A | | 9/2000 | Johnson et al. |
| 6,164,137 | A | | 12/2000 | Hancock et al. |
| 6,170,336 | B1 | | 1/2001 | Johnson et al. |
| 6,271,660 | B1 | * | 8/2001 | Sprecher, Jr. .......... 324/207.13 |
| 6,561,035 | B2 | * | 5/2003 | Passarelli, Jr. ............... 73/643 |

OTHER PUBLICATIONS

Bray, Don E. and Stanley, Roderic K. , *Nondestructive Evaluation, A Tool In Design Manufacturing, and Service*. Revised Edition. CRC Press Boca Raton, New York, London, Tokyo. 1997. pp. 382–385.

* cited by examiner

Primary Examiner—Hezron Williams
Assistant Examiner—Rose M. Miller
(74) Attorney, Agent, or Firm—Michael B. Brooks P.C.; Michael Blaine Brooks; Andrew S. Naglestad

(57) ABSTRACT

The disclosed invention mounts transmitting and receiving electrical coils within channels or chambers formed by the notched ends of magnets closest to the metallic object under test where the magnets are arranged to form substantially annular arrays of an electromagnetic acoustic transducer pair applicable in non-destructive testing. The detection, preferably by tuned coils, of one or more electromagnetically-induced resonant frequencies at shifted locations indicates the presence of one or more flaws in the metallic structure under test.

15 Claims, 13 Drawing Sheets

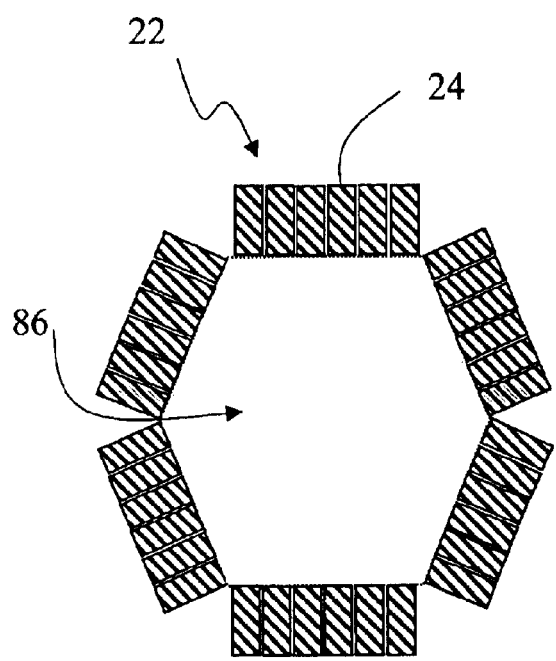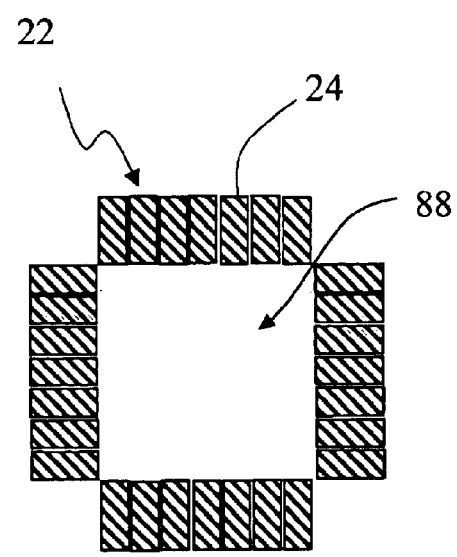
FIG. 5A  FIG. 5B

ELECTROMAGNETIC ACOUSTIC TRANSDUCER WITH RECESSED COILS

CROSS-REFERENCE TO RELATED APPLICATION

This application is a continuation-in-part of U.S. patent application Ser. No. 09/991,147, filed Nov. 13, 2001, now U.S. Pat. No. 6,561,035, titled ELECTROMAGNETIC ACOUSTIC TRANSDUCER WITH RECESSED COILS, by Frank Passarelli, Jr., which claims the benefit of Provisional Patent Application Ser. No. 60/248,991 filed Nov. 15, 2000, both of which are hereby incorporated herein by reference. This application is also a continuation-in-part of U.S. patent application Ser. No. 10/374,372, filed Feb. 25, 2003, now abandoned, titled RESONANT MODE EMAT COIL TUNING APPARATUS AND MATERIAL RECOGNITION METHOD, by Frank Passarelli, Jr., which claims the benefit of Provisional Patent Application Ser. No. 60/360,095 filed Feb. 25, 2002, both of which are hereby incorporated herein by reference.

BACKGROUND OF THE INVENTION

1. Technical Field

The field of this invention relates to electromagnetic acoustic transducers usable with substantially cylindrical objects, and methods for determining resonant frequencies and identifying physical properties, particularly flaws, of the substantially cylindrical objects using electromagnetic acoustic transducers with coils recessed into parallel arrays of magnets arranged in a radial fashion transverse to the longitudinal axis of the cylindrical objects.

2. Description of the Related Art

Inspections according to and as required by government regulations and industry standards are commonly performed on commercially manufactured products including steel and aluminum pipes and tubing and also including elongated, substantially cylindrical bar stock, such as those used in pressurized applications, and also including elongated, substantially cylindrical bar stock, such as those used in high torque applications, e.g., fastenings. The subjects of these regulations and standards are the qualitative and quantitative standards controlling the properties of materials, such as strength, granularity and the presence and severity of flaws.

Clearly, the presence of certain defects can adversely affect the safety and structural integrity of the finished product. It is therefore preferred that the flawed portions of these metallic stocks and commercially manufactured products be economically identified and removed with the flawed portions of these materials recycled. In addition, the need to correct and improve processes and machinery by identifying flaw-producing causal relationships motivates actions that subject the removed portions to further inspections prior to recycling.

It is well known that in the fabrication and refinement of metallic articles, the foundry process itself, as well as errant machinery and other equipment used in the fabrication and refinement can produce one or more unacceptable flaws in the product articles. Present common practice in accordance with current quality control programs places an entire production run subject to rejection due to flaws in a small, but statistically significant, number of parts. There exists economic motivation to detect such flaws directly and thereby indirectly identify one or more problems with the manufacturing equipment or process. Once identified and corrected, manufacturers may then work to minimize the future generation of flawed metallic structures as well as the magnitude of the rejected stock under test. Varying degrees of economic benefit may be gained by the use of various test techniques in ascertaining the location of a flaw and determining the type of flaw.

Presently, there exist a variety of test techniques available and known to practitioners in the field that manufacturers may implement separately or in combination to determine flaws in metallic structures. Generally, one may dichotomize these as destructive and non-destructive test techniques. In destructive testing, a selected portion of the subject metallic item is destroyed; a portion that could very well be flawless while the remaining unselected portions of the metallic part may contain numerous unacceptable flaws. The extensibility of the results of destructive testing of a portion of the metallic item to the remainder of the item can vary greatly.

The principal advantage of non-destructive testing is that the metallic structure is examined throughout with only the flawed portion being isolated and removed, thereby leaving the unflawed portion for immediate usage. Typically, once a flawed portion in the metallic structure is determined, the testing procedure and/or device employs some means to ascertain the location of that flaw and the metallic structure is marked accordingly. With respect to non-destructive test techniques, there is a wide range of technology available including the use of eddy currents, magnetic flux leakage, x-ray, ultrasound, neutron detraction, and so forth. Where commercially practical non-destructive testing is implemented, one skilled in the art typically places one or more of devices embodying at least one of these non-destructive technologies within the production line so as to ascertain a flawed portion of a particular metallic structure during the normal production of a metallic structure.

Practitioners in the field are generally aware of the use of acoustic resonance techniques in the non-destructive testing of metallic structures. The use of acoustic resonance can offer significant advantages over other prior art types of non-destructive testing technologies. However, acoustic resonance techniques of the prior art have met with limited success due to the difficulty and expense in applying such especially with the use of contact type transducers.

Contact-type transducers, by their mechanical nature, affect the intrinsic resonance of the metallic structure since such transducers, by necessity, come into mechanical contact with the metallic structure. The affect the testing device has on the metallic part under test leads to complex signal and processing schemes to account for the variation in resonance such as taught by U.S. Pat. No. 5,062,296 to Magliori and U.S. Pat. No. 4,976,148 to Magliori, et al. These inventions employ a ceramic piezoelectric transducer, one that is typically a contact-type of transducer. A non-destructive testing device that does not require contact with the metallic part under test would be preferred so that the metallic structures under test resonate in isolation and thereby forgo the complexities and uncertainties associable with the contact-type signal processing.

It is well known to those skilled in the art that non-destructive testing can be performed by electromagnetic acoustic transducer (EMAT) devices disclosed in U.S. Pat. No. 6,109,108 to Ohtani, et al., U.S. Pat. No. 6,164,137 to Hancock, et al., U.S. Pat. Nos. 5,895,856, 6,119,522 and 6,170,336 all to Johnson, et al. (collectively referred to as Johnson) and in U.S. Pat. No. 5,808,202 to Passarelli. Ohtani discloses burst wave technique with an apparatus using a sheet coil. Hancock discloses a technique for tubes using dual circumferential acoustic waves produced by a transmitting EMAT and sensed by a pair of receiving EMATs. Johnson and Passarelli disclose EMATs typically in arranged one or more planes of magnets of alternating polarities arrayed in a radial fashion about a substantially annular orifice or pass-through hole and transverse to the longitudinal axis of the substantially cylindrical object under test. Electrical wire is then positioned about each magnet array. Passarelli and Johnson disclose EMATs that can provide flaw detection at various levels within a metallic structure under test. This detection in depth offers significant advantages over Hancock when moving from tubular to substantially solid objects under test.

Passarelli discloses each plane pair, together with transmitting and receiving coils and signal processing, act as the transmitting and receive circuit and provide the fields producing the resonance frequencies in the metallic structures under test. Observations gathered from field trials in both steel and aluminum mills indicate that there is an unacceptable decrease in the distance from the metallic part under test to the transducer coils. That is, the gap distance is decreased for the larger sample sizes of metallic structures of one inch or greater in diameter or maximal transverse dimension, limiting the degree to which one may locate the transmitting and receiving coils in closest practical proximity to one another, as is done for smaller diameter metallic structures such as around one-eighth to three-eights inch in diameter. On the other hand, if the gap distance is practically minimized, the electrical benefit is that the field coupling into the metallic structure is maximized and the cross-talk leaking into an adjacent transducer is minimized.

Under typical milling conditions, a metallic structure such as a pipe or tube moves at around three hundred feet per minute relative to the transducer. In the course of ordinary milling condition, the metallic structure moves laterally, or wobbles, and it is this wobble, in practice, that causes the metallic structure to mechanically contact the transducer. That is, as the gap distance decreases, the metallic structure under test is at great risk of coming into contact with the transducer causing damage to the transducer and posing a hazard to mill operations. Thus, a disadvantage of Passarelli and Johnson is that one cannot both accommodate the larger stock and ensure, under continuous mill conditions, the safe passage of the material structure in conjunction with the transducer, because the gap distance from the metallic part to the transducer coil cannot be practicably decreased within the prior art to acceptable distances.

There is another disadvantage to the aforementioned prior art arrangement in that the geometry of the coil used in conjunction with the transducer has an aspect ratio, thin and wide, that naturally causes the solenoid coil to have a substantial field emanating from the coil ends along its Z axis. Increasing coil thickness to improve coil performance by tightening up the field produces marginal improvement. But the major disadvantage is that the magnets must be moved further away in order to accommodate the thicker coil. This is not a satisfactory tradeoff since the magnetic field provided by the magnets decreases as the square of the distance from the metallic structure.

An additional difficulty posed by the prior art EMAT structure is that in order to achieve a minimal level of direct coupled signal from the transmitter coil to the receiver coil, the coil turns count must be reduced to enable the coils to be spaced further apart, thus decreasing the defect size resolution. The path length over which the resonance sound field traverses is longer and therefore increase the material's volume under resonance.

In the field of ultrasonics impedance matching is commonly used on a variety of transducers primarily to improve signal to noise performance or to maximize transmitted power. Similarly, in the case of the resonance mode electromagnetic acoustic transducer the ability to selectively tune the impedance of the coil subassembly through a combination of coil construction and capacitative tuning dramatically improves the transfer impedance characteristics between the coil assemblies and the sample under test. This tuning process allows for optimization of signal to noise performance on a variety of materials with differing permeabilities and geometries such as hexagonal shapes.

This tuning process while not essential in all applications adds a margin of safety to the unique end of the sample detection method. Since the RM-EMAT method of generating and detecting sound waves within the test specimen allows for material's property measurement right up to the end of the sample a method to detect when there is sufficient material within the transducer to support resonance was required. Typically external proximity sensors are placed adjacent to the transducer to suppress the measurement system from processing data as the sample enters and exits the transducer, this eliminates false positives from being generated and the needless rejection of good material due to these end effects. However this also creates gaps in the measurement capability. A method has been developed to enable the transducer to "self-sense" the presence of material under test by monitoring the changing coil voltages caused by the changing coil impedances. The means to detect the end of the sample is described. Additionally, since the means and methods using proximity sensors require additional complexity and expense used with the present inventions, the ability of the transducer to self-detect whether or not material is present and properly coupled in the transducer is also of commercial value.

SUMMARY OF THE INVENTION

A non-destructive testing apparatus is disclosed comprised of a pair of EMATs; a first EMAT for the transmission and inducement of acoustic waves intended to establish resonances within the metallic structure under test and a second EMAT for the reception of the induced acoustical resonances. Each EMAT is comprised of an electrical coil mounted within a channel or chamber formed by the notched ends of magnets where said magnets are arranged to form an annular array in a radial fashion transverse to the longitudinal axis of the metallic structure under test. The novel recessed mounting of the coils provided by the channels or chambers substantially reduces the observed electrical cross-talk between coils over the prior art and reduces the likelihood of the coils making contact with the subject metallic structure under test while the metallic structure is in longitudinal motion relative to the coils.

In practice, a particular reference resonant frequency is known or can be calculated for an unflawed metallic structure. The transmitting coil is supplied power which when combined with the force of the magnets will cause the metallic structure to vibrate within a range that is to include a resonant frequency. As the magnetic structure passes relative to the transducers and when a flaw is detected, the resonant frequency is shifted out of the range established for an unflawed metallic structure. This shifted resonant frequency can be above the range or below the range for the unflawed metallic structure. The induced resonant frequency of the metallic structure is sensed by the receiving transducer and then by a voltage/current sensor, such as an AM detector, transmitted via an analog-to-digital converter to a computer. Associated with the transmitting transducer and receiving transducer pair is some form of optional marking device that is capable of marking the metallic structure at the point of the flaw once the resonant frequency of the flaws portion exceeds the unflawed range as determined by the computer.

The subject matter of this invention is constructed so that each array of magnets located in conjunction with each transducer has a channel, or chamber formed therein. Within this channel is located an electrical coil. This placement of the electrical coil is different from prior art where the coil was mounted on the exterior surfaces of the magnets closest to the metallic structure under test. This novel accommodation and placement of the coils within the channel or chamber formed by the magnets of the transmitting transducer and the receiving transducer: (1) permits the transmitting transducer and receiving transducer to be enclosed within a single housing and located in close proximity to the metallic structure being tested and (2) substantially reduces the cross-talk between the transmitting transducer and the receiving transducer.

The advantages of using the construction of the transducers of this invention are as follows: (1) with respect to aspect ratio, the coil aspect ratio can now be altered making the coil thicker and narrower without moving the permanent magnet array farther from the metallic structure (i.e., the same coil winding density, or turns ratio, is maintained and therefore, the coil's inductive properties can better match those of a wider coil design); (2) with respect to tighter acoustic field dispersion, the narrower coil now produces a narrow acoustic field that is generated by the transmitter transducer and the channel within which the coil is mounted can be moved so as to maximize the detection resolution depending upon measurement requirement; (3) with respect to solenoid coil side lobe reduction, the solenoid coil that is mounted within the channel of the magnets significantly reduces cross talk, (i.e., the electromagnetic signal that directly couples from the transmitting transducer into the receiving transducer) and this mounting of the coil within a channel of the magnets effectively provides a shield to reduce this cross-talk by a factor greater than ten from prior art structures such as disclosed in U.S. Pat. No. 5,808,202 to Passarelli; (4) with respect to magnet lift-off distance, the channeled magnet structure of this invention decreases magnet lift-off distance by bringing the edges, or skirts of the magnets, closer to the metallic structure being tested by a factor equal to the coil thickness and thereby strengthens the direct current bias field supplied by the magnets by a factor of square of the distance although the magnets and coil are not inline with each other at these skirts and the additional field provided by the magnets improves transduction efficiency; (5) with respect to coil protection, the soft coil is now recessed into the relatively hard magnet skirt providing added protection from coil impact damage due to possible contact of the coil by the metallic structure under test; and (6) with regards to multi-frequency operation from a single transducer, with coil impedance properties being stabilized, it becomes practical to drive a single transducer at multiple frequency bands, resulting in a single transducer transmit and receive pair capable of inspecting multiple sample cross-sections or depths.

Described herein is a method for dramatically improving the signal-to-noise characteristics of the RM-EMAT. The turns ratio of the coil, that is the gauge of the wire and the number of layers of this coil (for both transmitter and receiver or a single coil operating as a transceiver) are designed such that the frequency of natural electrical reactance of the coil, when loaded with the specimen under test, are close to the chosen acoustic resonant frequency. Since it is impractical to wind such a coil assembly so that one would have the exact number of turns of wire to properly match the electrical resonance with the acoustic resonance, tuning means comprising the placement of a small value tuning capacitor in parallel, electrically, with the coil, is disclosed. This placement of the small value tuning circuit forms a parallel tuned circuit as the tuning means that adjusts the coils' electrical reactance, i.e., maximizing the real impedance term, R, and minimizing the imaginary impedance term, J, to peak at the desired acoustic frequency. An additional beneficial effect provided by the tuning of the coil enables the transducer to sense whether or not a test specimen is present in the transducer.

The method described herein is the signal processing method utilized in the resonance mode electromagnetic acoustic transducer based measurement system. This acoustic resonance measurement system (ARIS) is closed loop device where a microcomputer controls signal generation, post demodulation analog or digital signal processing and control signal input/output. Operating as a continuous sweep (CW) system the microcomputer generates the data set that contains the start/stop frequencies. Signal generation and detection is a synchronous or in effect a closed feedback loop. Each generated frequency point is simultaneously captured by the receiver and analog to digital converter prior to progressing to the next step in the preprogrammed frequency sweep. These frequency sets are typically narrow band approximately 3 to 30 kHz in bandwidth. These narrow bandwidths provide a balance between adequate detection sensitivity of small frequency deviations, from the normal material resonant frequency, that are typically generated by small anomalies in the sample under test, and sufficient bandwidth for maintaining a high overall system speed. Also in order to achieve sweep rates that will support high throughput speeds of the material under test the demodulation and error detection technique must be kept as simple as possible arithmetically.

Shifts or decays in the resonant frequency indicate anomalies interspersed through the volume of the sample as referenced to a resonant signal generated by a known sample without defects. However, extensive testing has indicated that a calibration sample is not required since the change in frequency is directly related to anomaly volume versus sample volume for a given transducer.

BRIEF DESCRIPTION OF THE DRAWINGS

For a more complete understanding of the present invention and for further features and advantages, reference is now made to the following description taken in conjunction with the accompanying drawings, in which:

FIG. 5A illustrates a hexagonal array of permanent magnets in transverse view of permanent magnets of the present invention;

FIG. 5B illustrates a rectangular array of permanent magnets in transverse view mounted in a substantially circular array having a substantially flat perimeter across a sector;

DETAILED DESCRIPTION OF THE PREFERRED EMBODIMENT

Figure 1:
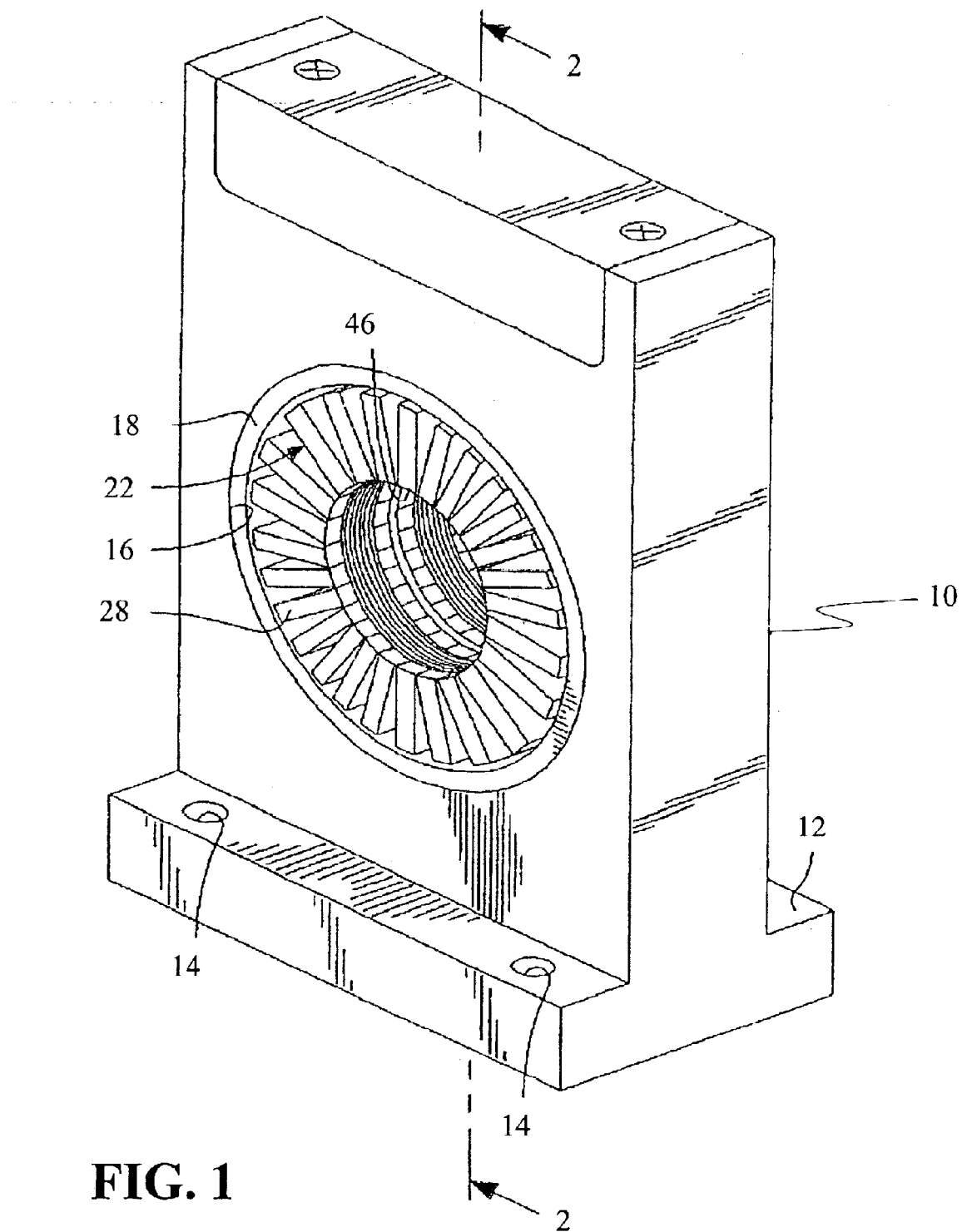
FIG. 1 is an isometric view of the transducer assembly of the present invention which comprises a transmitting transducer and a receiving transducer mounted in conjunction with a single housing.

The present invention, in its several embodiments, uses transmitting and receiving electrical coils mounted within channels or chambers formed by notched, grooved or otherwise channeled ends of magnets closest to the metallic structure or object under test where the magnets are arranged to form substantially arrays about the metallic object under test, preferably using an EMAT pair. The detection of one or more electromagnetically-induced resonant frequencies at shifted locations indicates the presence of one or more flaws in the metallic structure under test. The use of the EMAT pair permits continuous scanning along the axis of an elongated metallic structure thus giving the flaw detection apparatus of this invention utility in nondestructive testing without the need for physical contact of the object under test by the testing unit. Because the EMAT is intended to not contact the metallic part, distortion is thereby minimized, except for accidental contact, which would be caused by the mechanical impedance mismatch endemic to the contacting method of ultrasonic resonance generation. The use of an EMAT enables a precise segmented range or scan of vibrational frequencies of the metallic structure and its wave mode selectivity minimizes the generation of parasitic acoustic vibrations that may dilute the frequency resolution of the flaw detection system.

The use of an EMAT for the generation and detecting of resonances within metallic structures is radically different from other ultrasonic flaw detection systems. EMATs effectively address the issues of the prior art that have hindered the use of acoustic resonance in non-destructive testing. Using an EMAT for the generation of acoustic resonance provides a signal fidelity advantage of several orders of magnitude over all other known types of ultrasound-based flaw detection apparatuses.

Operation of the system of the present invention takes full advantage of resonance principles. The operator, after selecting and installing the appropriate size and shape of the transducer for the given application, enters the type of material and its shape preferably into a computing or processing device. The processing then determines the range of frequencies that should be subjected to the metallic structure in order to obtain a resonant frequency for the metallic structure when in an unflawed condition. The processing preferably controls the frequency scans through the selected range of the transducer driving electronics. The processing continues with executing, preferably via analog electronics, a repetitive search for resonation based upon a predictive calculation of the frequency at which the metallic structure is expected to resonate. Once resonance is established, the acceptable frequency deviations for both the unflawed condition and the flawed condition for a defect are then established and then sequential frequency scans can then proceed. In the preferred method of use, the range of resonant frequencies is set for what is determined an unflawed metallic structure thereby establishing the acceptable limits of an unflawed condition in the metallic structure. This frequency scanning rapidly divides the axis of the metallic structure under test, in the case of tubular goods or the like, into identifiable segments thus providing the ability to locate the position of any anomaly along the longitudinal axis of the tubular goods. The operator or an automated system can then mark the flaw location while the testing process continues. Accordingly, no stopping of the metallic structure is required during the test procedure.

The principles of operation of the flaw detection apparatus of the present invention have specific utility in determining of flaws in cylindrical shapes. However, it is to be understood that the structure of this invention is not intended to be limited to only cylindrical shape geometry. For example, objects under test having oval, elliptical, polyhedral shapes in transverse including without limitation complex shapes such as circles with flat sector portions may be satisfactorily subject to the nondestructive testing device and methods of the several embodiments of the present invention. Every metallic structure whose material and structural qualities are considered sound or normal will have vibrational modes that produce resonant frequencies that fall within a typical domain. Resonant behavior outside of that domain represents some range of anomalies that indicate the presence of a qualitative or quantitative defect.

In the specific case of generating vibrational modes in tubes and rods, these types of structures are mathematically treated as uniform cylinders of infinite length. While the structures under test may not fit the exact structure of a uniform cylinder of infinite length, a reasonably accurate prediction can be obtained at those frequencies the structure will resonate. The type of vibrational energy used in conjunction with this invention for flaw detection in rods, tubes and other objects under test includes axial shear or axial shear-like wave modes. Their wave vector in the azimuthal direction characterizes these axial shear vibrations. The particle motion along the axial direction comprises an integral number of wavelengths around the circumference of the rod or tube. Therefore, the number of magnets incorporated within the transducer determines the number of integral wavelengths around the circumference of the rod or tube.

In order to determine the approximate frequency of resonance the following equation is used:

$$F = \frac{BV}{2\pi R};\quad [1]$$

where F represents the frequency of resonance, B represents a root value of a Bessel function of the second order, V represents the velocity of sound of a horizontal shear wave in the metallic structure and R represents the radius of the metallic structure. Within each EMAT of a preferred embodiment of the present invention, twenty-six individual magnets produce thirteen wavelengths. For example, where the metallic structure comprises an elongated length of 6061 aluminum rod having a diameter of 25.4 millimeters and a sound velocity (V) of 3.04 millimeters per microsecond, the first five solutions for B are shown in the following table with the resulting frequency for resonation corresponding to each frequency. The location as to what portion of the aluminum rod these resonations occurs is also noted.

TABLE

| B | F | Approximate Scan Depth |
|---|---|---|
| 14.928374 | 576.901 KHz | From surface of rod to around .20 inches deep |
| 19.883224 | 768.380 KHz | Below surface at and around .35 inches deep |
| 23.819389 | 920.491 KHz | Below surface at and around .46 inches deep |
| 27.47434 | 1,061.736 KHz | Below surface at and around .54 inches deep |
| 30.987394 | 1,197.497 KHz | Below surface at and around .60 inches deep |

The above table indicates that if the resonant frequency is determined to be around 576 KHz, flaws will be detected in the outer layer of the aluminum rod. At a frequency of about 768 KHz, flaws will be detected below the surface of the aluminum rod around a depth that corresponds to a diameter of 0.65 inches of the rod or tube. At a frequency of 920 KHz, flaws will be detected again below the surface of the rod around the depth of 0.54 inches in diameter. Similarly, at a frequency of 1,061 KHz, flaws will be detected below the surface of the rod around 0.46 inches in diameter. Finally, at a frequency of 1,197 KHz, flaws will be detected below the surface of the rod around 0.40 inches in diameter.

It is to be understood that the above-referenced resonant frequencies, in addition to being influenced by the presence of defects, are influenced by variances in alloy composition, temperature, and the diameter of the rod. The effect on resonance caused by the presence of defects presents a significantly different effect on the frequency than other influences. The presence of defects causes the resonant signal to shift position in an abrupt manner. This shift in frequency is due to a decrease in the velocity of the sound being propagated through the rod. The velocity (V) of sound in a solid for a shear wave is determined by the following equation:

$$V = \frac{\sqrt{\mu}}{\rho};\quad [2]$$

where $\mu$ represents the internal stress and $\rho$ represents the mass density. The internal stress, $\mu$, is substantially affected in the vicinity of the flaw and it is reflected in the resonant frequency.

Referring again to the above table, for the user to discover flaws at the surface level of the metallic structure, it would only be necessary to use an EMAT that is preset to the range of around 576 KHz. However, the EMATs of the present invention provide for the simultaneous determination of flaws in the metallic structure at deeper depths. That is, the EMATs can additionally operate in the range of 768 KHz to detect flaws at and around 0.35 inches below the surface of the metallic structure, in the range of 920 KHz to detect flaws at and around 0.46 inches below the surface of the metallic structure, and other higher frequency ranges to provide the user with flaw detection data substantially through the entire metallic structure.

Figure 2:
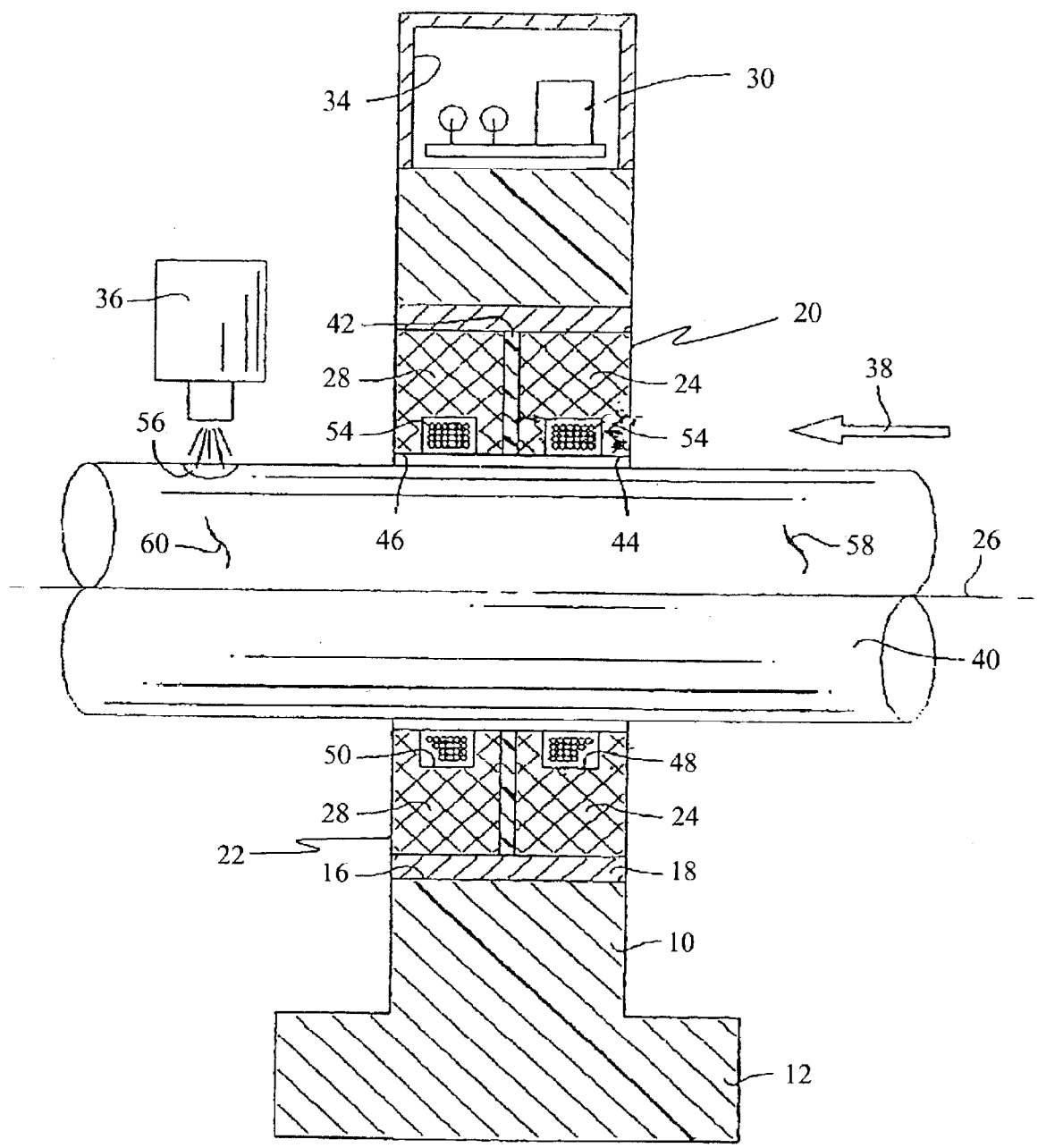
FIG. 2 is a transverse cross-sectional view through the transducer assembly of FIG. 1 taken along 2—2 of FIG. 1.

Referring particularly to the drawings, FIG. 1 illustrates an example of a housing 10 that houses the flaw detection apparatus of this invention. FIG. 2 illustrates the housing from the perspective of a transverse cross-sectional view through the transducer assembly of FIG. 1 taken along 2—2 of FIG. 1. The housing 10 includes an optional base 12 mountable to on an exterior structure by using bolt-type fasteners working in conjunction with holes 14. The housing 10 includes a pass-through opening 16. Mounted within the pass-through opening 16, in a snug fitting manner, is a steel sleeve 18. Mounted within the confines of the steel sleeve 18 are a first series of magnets 20 and a second series of magnets 22. It is understood that the term magnet refers to permanent magnets and to ferrite materials and otherwise magentizable materials applied separately or in combination to form an article. The first series of magnets 20 includes a plurality of first series magnets 24 and the second series magnets 22 includes a plurality of second series magnets 28. In the preferred embodiment, there are twenty-six in number of first series magnets 24 each of which assumes a radial and substantially evenly spaced position relative to a longitudinal center axis 26. The number, composition and orientation of the first series magnets 24 can vary with specific applications. The longitudinal center axis 26 passes through the center of the pass-through opening 16. The first series magnets 24 complete an entire substantially circular pattern, or array, and each of the first series magnets 24 are substantially of the same size and composition. Every other magnet in the first series of magnets 20 are arranged so that the north and south poles of a particular first series magnets 24 are reversed relative to a immediately adjacent magnet of the same series. That is, the first series magnets 24 are in an alternating polarity (north-south) array. The second series magnets 28 of the preferred embodiment are also twenty-six in number. As with the first series magnets 24, the number, composition and orientation of the second series magnets 28 can vary with specific applications. The second series of magnets 22 are preferably located in juxtaposition to the first series of magnets 20, in arrays of substantially parallel planes. The second series magnets 28 are not axially aligned with the first series magnets 24 but are instead angularly displaced, that is axially rotated from alignment, a few degrees from one array to the other. In practice for two twenty-six magnet substantially circular arrays, this angular displacement amounts to about 6.92 degrees as each of the first series magnets 24, when comprised of twenty-six in number, is located about 13.846 degrees apart from one another, the same displacement also being true for second series magnets 28.

The first series of magnets 20 and the second series of magnets 22 connect electrically to appropriate electronic components 30 which are contained with a compartment 34 of the housing 10. These electronic components 30 connect appropriately to necessary operating structures, such as a computer (not shown). In one embodiment, the computer drives a marking device 36, such as a spray painting mechanism, mounted close to, but just downstream of, the housing 10 relative to the path of travel represented by the directional arrow 38 of the metallic tubular structure 40. Under typical milling conditions, the metallic tubular structure 40 passes through the pass-through opening 16 at about three hundred feet per minute. Other objects under test may move at rates other than that of the metallic tubular structure 40.

Between the first series of magnets 20 and the second series of magnets 22, there is a dielectric spacer 42. The function of the spacer 42 is to fixedly establish the spacing between the first series of magnets 20 and the second series of magnets 22. This spacer 42 acts to further minimize the conducted and induced electromagnetic fields generated by and in the coil/magnet structures. Since the near field electromagnetic properties are the predominant form of mutual coupling between the array assemblies the spacer is constructed such that it shunts to ground the electric field emanating from the magnet arrays. These fields are generated by the high frequency eddy currents created in the magnets by the coil assemblies in spite of their relatively high dielectric constants. The spacer 42 is preferably of the same height, relative to the radius, as the height of the magnet skirts at the first inner pass-through opening 44 and at the first inner pass-through opening 46, thus providing a maximal reduction of side lobe radiation. A further advantage in maintaining this spacer height is to reduce to an absolute minimum the axial distance required between the adjacent array structures. Secondly the space surface of the spacer 42 is covered with an insulating layer to prevent direct coupling of these currents into the spacer 42 and thus turning the spacer into a field conduit.

The inside surfaces of the first series magnets 24 form a circularly shaped first inner pass-through opening 44. Alternative embodiments of the first inner pass-through opening exist to better effect an optimal distance between the first series of magnets and the object under test where the first inner pass-through opening shapes are by example and not limitation, include an elliptically-shaped first inner pass-through opening; an oval-shaped second inner pass-through opening; a substantially circular first inner pass-through opening having a flat sector; and polyhedron-shaped first inner pass-through openings including hexagonal and rectangular shapes, for example. Similarly, the inside surfaces of the second series magnets 28 form a circularly-shaped second inner pass-through opening 46. Alternative embodiments of the second inner pass-through opening 46 include an elliptically shaped second pass-through opening and substantially circular second pass-through opening having a flat sector. Alternative embodiments of the second inner pass-through opening 46 are used to better effect an optimal distance between the second series of magnets 28 and the object under test where the second inner pass-through opening 46 shapes are by example and not limitation, include an elliptically-shaped second inner pass-through opening; an oval-shaped second inner pass-through opening; a substantially circular second inner pass-through opening having a flat sector; and polyhedron-shaped second inner pass-through openings including hexagonal and rectangular shapes for example. The inside surfaces of the first series magnets 24 each include a recess so there is formed a substantially continuous first substantially annular channel or chamber 48. For purposes of creating the recess or annular channel or chamber for the coil, it is understood that the term notch is used to represent a modification to each magnet whereby material is added to or removed from each magnet. A similar substantially continuous second substantially annular channel or chamber 50 is formed within the inside surface of the second series magnets 28. Mounted within the first substantially annular chamber 48 is a transmitting coil 52. Mounted within the second substantially annular channel or chamber 50 is a receiving coil 54. The transmitting coil 52 and the receiving coil 54 each comprise a coil spool on which is wound wire. Each of the wires of each coil 52 and 54 terminates in a pair of leads (not shown). These leads (not shown) connect to the electronics 30. The wires of the coils 52 and 54 typically comprise copper wire of a very small diameter. The size of the wire is variable with the particular size being selected preferably in accordance to individual desires and specific applications. The transmitting coil 52 and first series magnets 24 comprise the transmitting transducer, and the receiving coil 54 and second series magnets 28 comprise the receiving transducer.

Given the parameters for detection of flaws, real-time computer processing in conjunction with the transmitting transducer and the receiving transducer are used to detect flaws, such as first sample flaw 58 and second sample flaw 60 within the metallic structure 40. In one embodiment, a computer transmits an output signal to a programmable signal generator (not shown). The purpose of the signal generator is to generate a sweeping sine wave upon command from the computer. The signal generator transmits its output to an amplifier (not shown). The amplifier transmits the amplified signal to the transmitting transducer comprised of the first series of magnets 20 and the transmitting coil 52. For example, a sweeping or scanning of the signal between 586 KHz and 588 KHz occurs that results in the production of a sound flawed frequency spike when a flaw is present. The receiving transducer, comprised of the second series of magnets 22 and the receiving coil 54, detects the sound flawed frequency spike. The receiving coil 54 supplies the detected signal to an amplifier (not shown). From the amplifier, the signal is subject to phase and/or amplitude demodulation (i.e., an AM detector). For example, a diode rectifier (not shown) converts the signal from a sine wave to a DC voltage. The diode provides an output signal to an analog-to-digital converter (ADC) (not shown) that in turn transmits the signal to the computer. In addition, a counter timer (not shown) receives the output of the signal generator. The counter timer circuit synchronizes the activity of the signal generator and the ADC by keeping an accurate count of the number of cycles of each frequency step and recording precisely where and when each step occurs in the scan. If the electromagnetic acoustic transducer-based apparatus of the present invention detects a surface flaw, such as second sample flaw 60, the spiked, or otherwise peaking, area of the frequency will shift with this shift being outside an unflawed frequency area, such as 587.2 KHz. The computer will then document that detected flaw and, where the optional marking device is used, will appropriately cause the marking device 36 to be activated to apply a quantity of paint 56 onto the metallic structure of object 40 in alignment with the flaw 60. Alternate detection indicators include audio alarms, lights, and the like as well as database storage of flaw according to the kind of object under test. In the paint indicating embodiment, the region of the application of the paint 56 corresponds substantially with the location of the detected flaw in the metallic structure 40. By this marking, the detected flaw becomes apparent to the manufacturer manufacturing the metallic structure 40. That is, the present invention alerts the manufacturer through the marking of the metallic structure 40 with the paint 56 and thereafter, the manufacturer may choose to avoid immediate use of the flawed area. The same detection and marking procedure occurs for subsequent flaws as they present themselves as shifted resonant frequencies. In other applications of the several embodiments of the present invention, the metallic object 40 is submitted in lengths less than those of standard mill stock including industrial fastener lengths and the metallic object can be selected from individual fasteners having a longitudinal axis submitted serially along each of their longitudinal axes for testing.

Figure 3A:
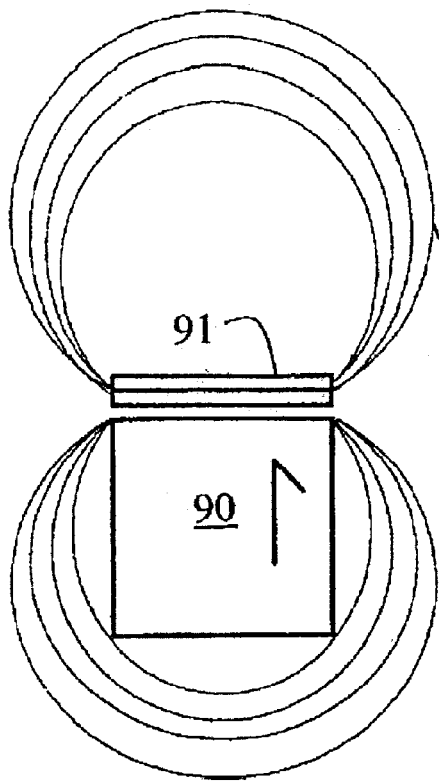
FIG. 3 illustrates the improved field characteristics of the present recessed coil, FIG. 3B as compared with the prior art, FIG. 3A.
Figure 3B:
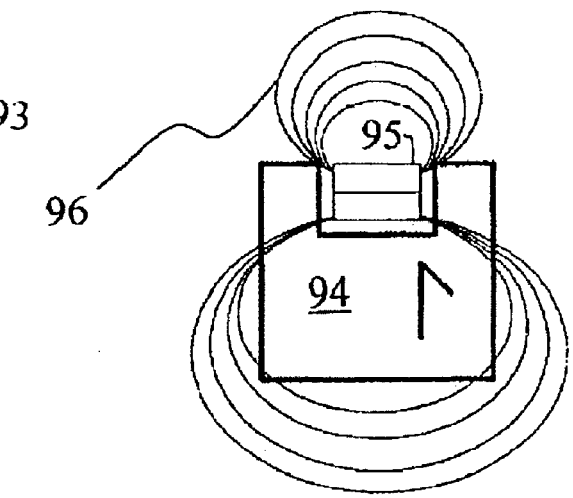

FIG. 3 illustrates, in a transverse view, the solenoid coil side lobe reduction from the side lobes of the prior art 93 in FIG. 3A to the side lobes of the present invention 96 in FIG. 3B. The prior art as disclosed by Passarelli in U.S. Pat. No. 5,808,202 and by Johnson in U.S. Pat. No. 5,895,856 mounts the coil 91 on top of each magnet 90, that is, on the edge of the magnet closest to the metallic structure under test (not shown). As explained above, this mounting of the coil 95 within a channel formed by the notch of each magnet 94 effectively provides a shield for the mounted coil that significantly reduces coil-to-coil cross-talk (e.g., a cross-talk reduction factor greater than ten from prior art structures) by reducing the side lobes 96.

Figure 4A:
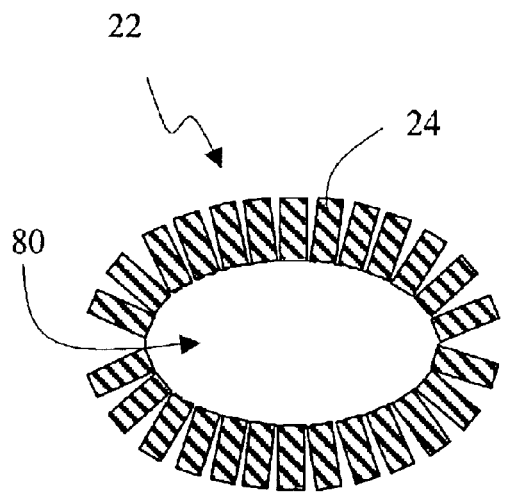
FIG. 4A illustrates an oval array of permanent magnets in transverse view of permanent magnets of the present invention.
Figure 4B:
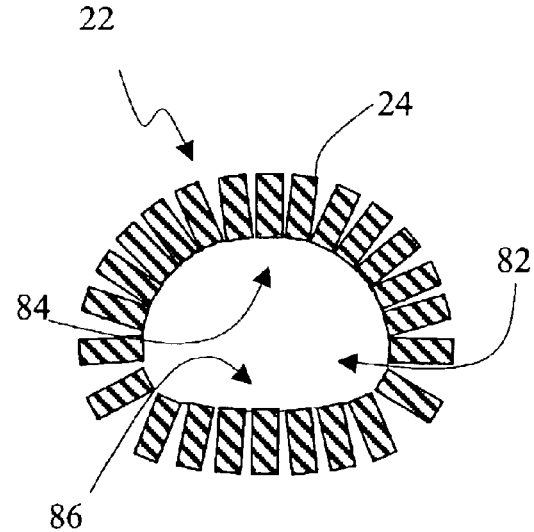
FIG. 4B illustrates an array of permanent magnets in transverse view mounted in a substantially circular array having a substantially flat perimeter across a sector.

The following embodiments are additional examples of the present invention having pass-through openings shaped to accommodate the series of magnets 22 and the sleeve 18. FIG. 4A illustrates in transverse view a series of magnets 22 arranged as an oval-shaped boundary of an inner pass-through opening 80 where the notched end of each magnet 24 is aligned substantially perpendicular to the local tangent of the oval-shaped boundary 80. FIG. 4B illustrates in transverse view a series of magnets 22 arranged about an inner pass-through boundary 82 having a circular portion 84 and a substantially flat portion 86 across a sector of the inner pass-through boundary 82.

FIG. 5A illustrates in transverse view a series of magnets 22 arranged around a hexagonal boundary of an inner pass-through opening 86 where the notched end of each magnet 24 is aligned substantially perpendicular to the local perimeter of the hexagonal boundary of the pass-through opening 86. FIG. 5B illustrates in transverse view a series of magnets 22 arranged around a rectangular boundary of a pass-through opening 88 where the notched end of each magnet 24 is aligned substantially perpendicular to the local perimeter of the rectangular boundary of the pass-through opening 88. These embodiments, as examples of the present invention, illustrate the pass-through opening can be is shaped to accommodate the series of magnets 22 and the sleeve 18.

Figure 6D:
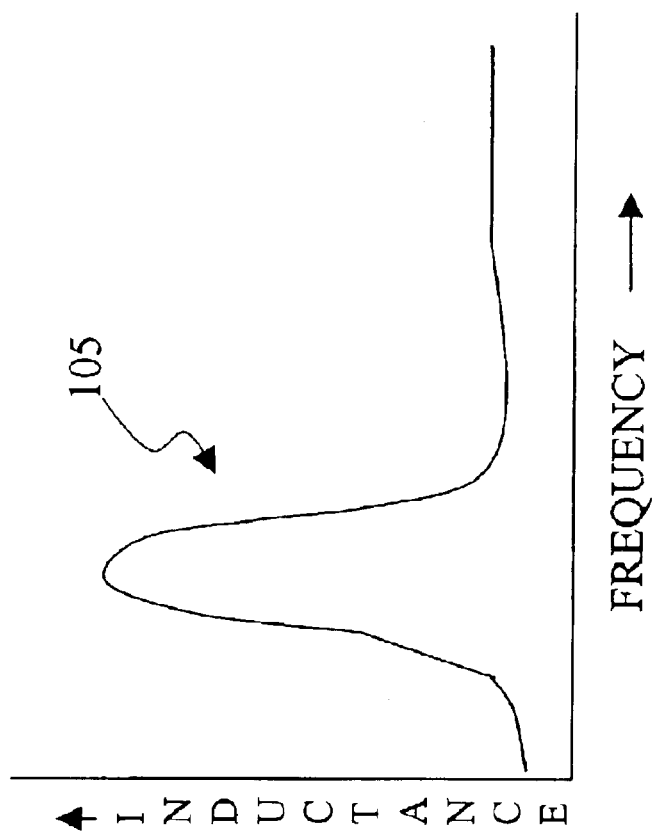
FIG. 6D illustrates a resonance of a coil in free space.
Figure 6A:
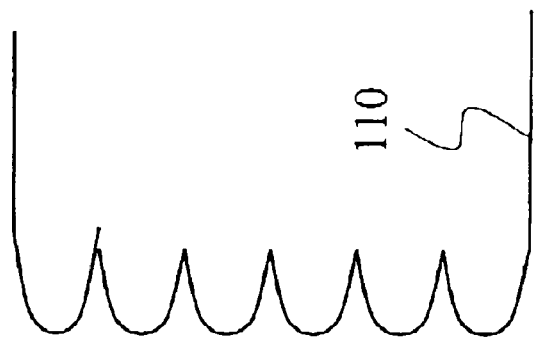
FIG. 6A illustrates a coil in free space.
Figure 6E:
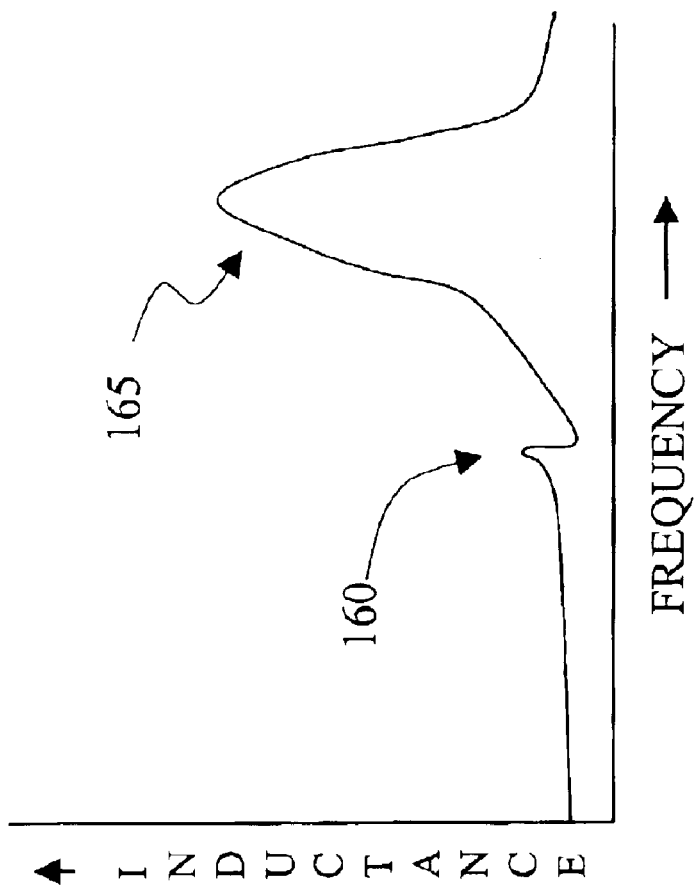
FIG. 6E illustrates a resonance of a coil in electrical proximity with a test specimen.
Figure 6B:
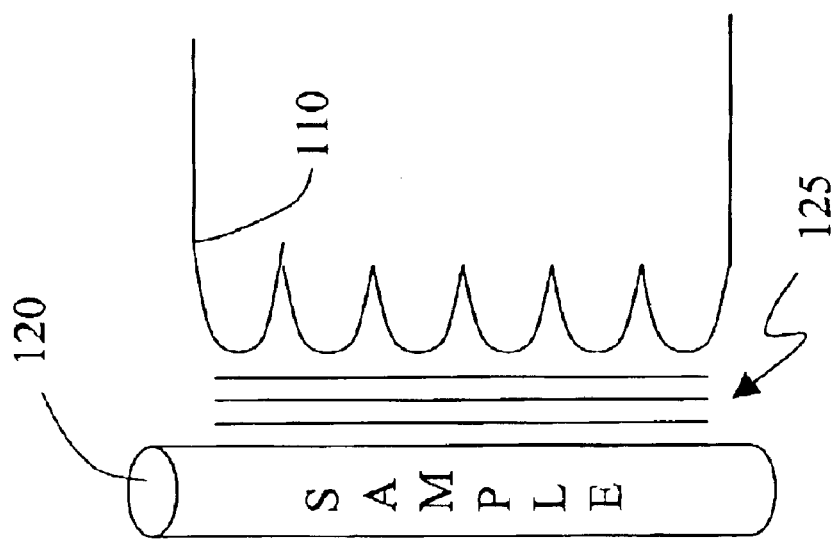
FIG. 6B illustrates a coil in electrical proximity with a test specimen.
Figure 6F:
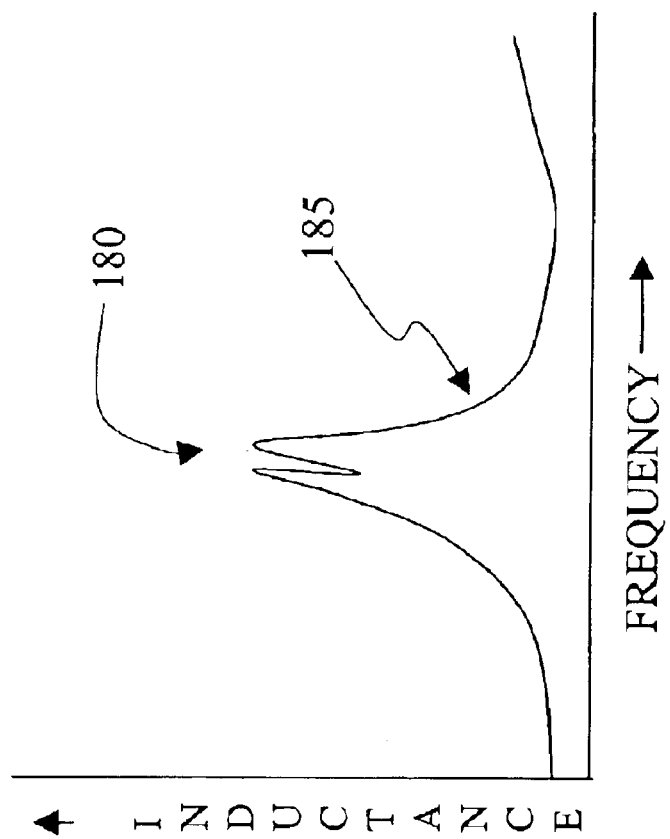
FIG. 6F illustrates a resonance of a coil in parallel with a tuning capacitor and in close proximity with a test specimen.
Figure 6C:
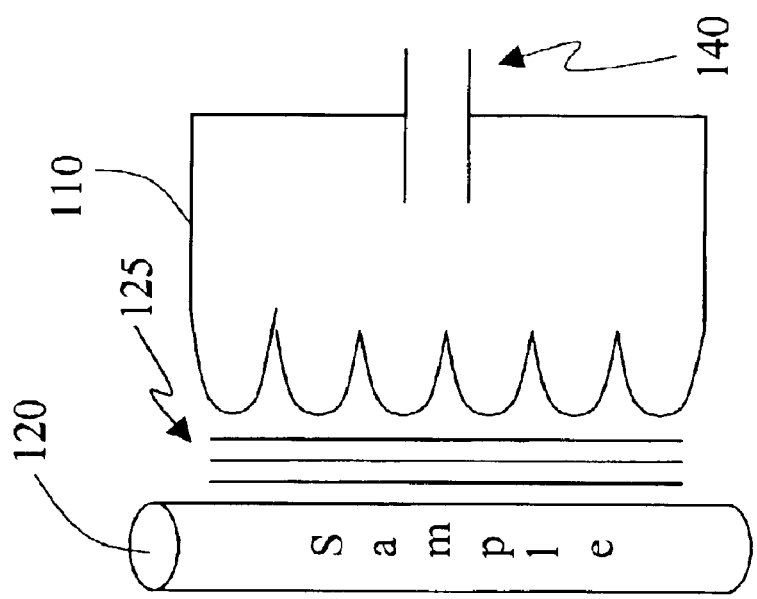
FIG. 6C illustrates a coil in parallel with a tuning capacitor and in close proximity with a test specimen.

An example procedure for fabricating the tuning means and the tuning method of a transducer coil according to the several embodiments of the present invention is described in the specific case as follows but is not restricted to the case of a solenoid winding configuration only. The solenoid coil can be mathematically modeled and those skilled in the art are well versed in determining the inductive properties of a closely wound multilayer cylindrical coil operating in both shielded and unshielded cases. The principal factors that tend to complicate modeling of the performance of the inductor include the conditions of the effective shielding in several industrial applications. That is, the transducer's magnet assembly surrounds the outside diameter of the coil, lowering the inductance and thereby increasing the reactive frequency. Tests indicate the decrease in inductance from free space to the value after insertion into the magnet array to be in excess of 75%. A second variable affecting coil performance is the insertion of a test specimen into the transducer (i.e., the magnet-coil) assembly, where the inductance is again reduced significantly and with the amount of this change varying with material type, diameter, shape and the surface condition of the object under test. In total, the reduction in inductance from the free space design approaches 90%. FIGS. 6A–6F graphically depict the impedance modification caused by such structure within the presence of a radio frequency coil of this type. FIGS. 6A–6F respectively illustrate a resonance 105 of a coil 110 in free space, a resonance 165 of a coil 110 in electrical proximity with a test specimen 120 further illustrating flux lines 125, and a resonance 185 of a coil 110 in parallel with a tuning capacitor 140 and in close proximity with a test specimen 120 and further illustrating flux lines 125. FIG. 6E illustrates an example acoustic resonance effect 160 upon the coil reactance at a frequency lower than the resonance peak. FIG. 6E illustrates an example acoustic resonance effect 180 upon coil reactance at or around the frequency of the resonance peak.

Figure 7:
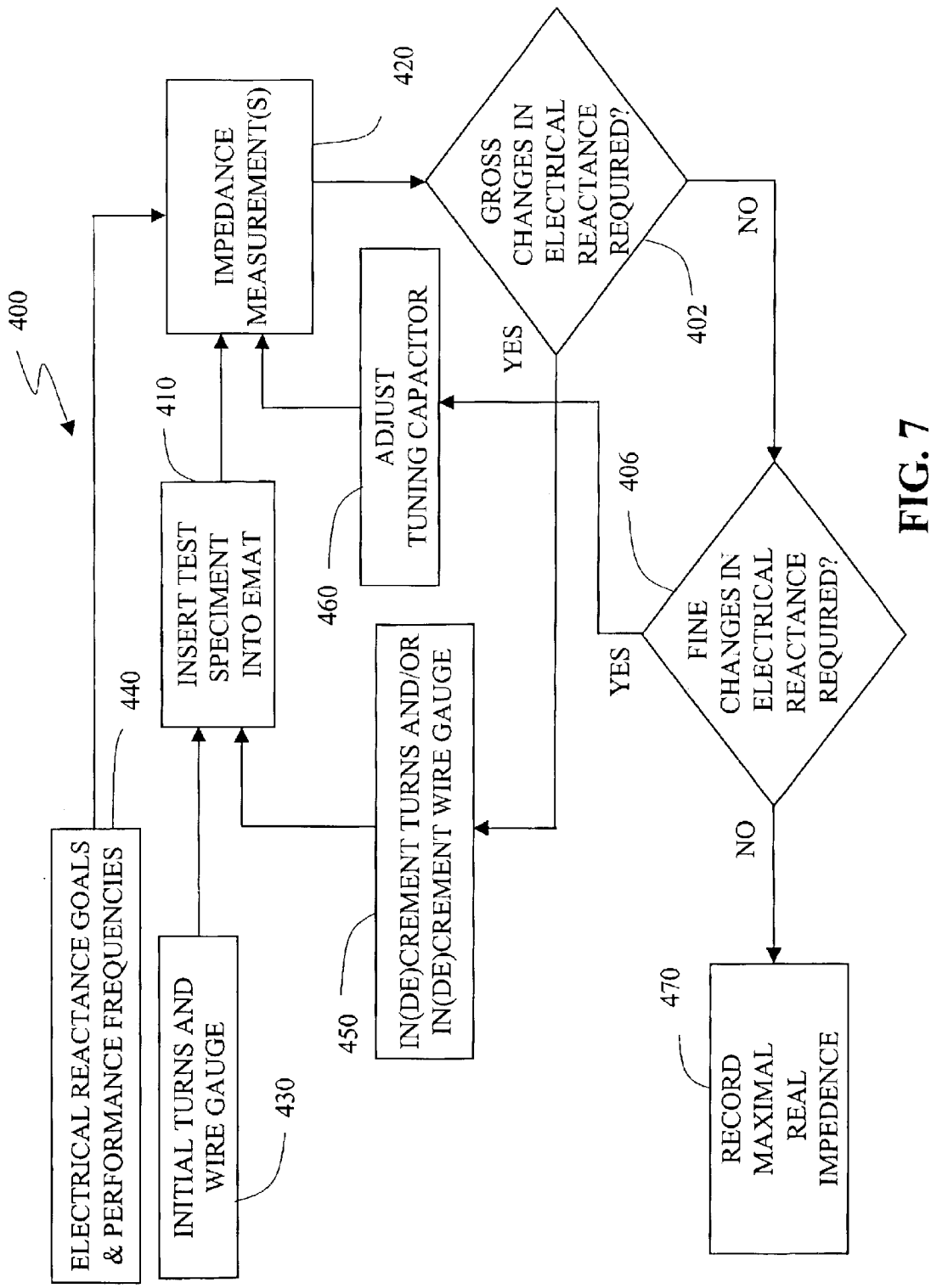
FIG. 7 is a flowchart illustrating the tuning process.

A coil 46 is wound to fit within the magnet array structure 22 as depicted in the example illustrated in FIG. 1. This coil 46 is fabricated with several layers of a selected gauge of insulated magnet wire, typically the type utilized to wind high-frequency inductors. Care is taken to wind such coil so as to keep the parasitic capacitance to a minimum. Additionally, electrostatic shielding may also be employed to reduce unwanted mutual coupling between the array assemblies. Performance test of the coil 46 is then performed by testing the coil 46 on an impedance analyzer or similar device capable of electrically driving the coil 46 at the frequencies where the coil 46 is expected to perform as part of an electromagnetic acoustic transducer at mid to high ultrasonic frequencies. This complex impedance measurement is performed with the desired test specimen inserted into the transducer with the desired outcome being a coil 46 with sufficient turns and wire gauge construction to maximize the electrical reactance at the required acoustic frequency. FIG. 7 illustrates that this process 400 may involve several coil design, fabrication and test iterations with the final step involving the addition of a small value capacitor, e.g., several picofarads, in an electrically parallel fashion to further increase the impedance at the desired frequency. This capacitor must be kept to a small value, i.e., a few picofarads, since the capacitor and its placement act as a signal shunt across the coil. With the wire gauge and initial turns of wire for the coil established 430 and with electrical reactance goals and performance frequencies established 440, the specimen is inserted 410 into the EMAT and impedance measurements are taken. Gross reactance comparisons are made 402. If gross changes in electrical reactance are required, the specimen is removed and the gauge and turns of the wire are changed 450 and the specimen is reinserted and the process iterates with impedance measurement 420. If gross changes in electrical reactance are not required, then fine reactance comparisons are made 406. If fine changes in the electrical reactance are required, then the tuning capacitor is adjusted and the process continues with impedance measurements 420. If no fine changes in electrical reactance are required, the maximal real impedance is recorded 470.

This tuned coil assembly also provides to basis for a convenient end of sample recognition method. There is a significant change in coil impedance that occurs when the sample is either in or out of the transducer; thus this effect is utilized as part of a feedback loop controlling system operation. This impedance change also produces a significant increase in voltage sensed at the receiver corresponding to a reduction in coil reactance. The implementation of a circuit that senses this voltage change and then generates a digital signal level corresponding to this change caused by the loading state of the transducer can be accomplished with the embodiment disclosed below.

Figure 8:
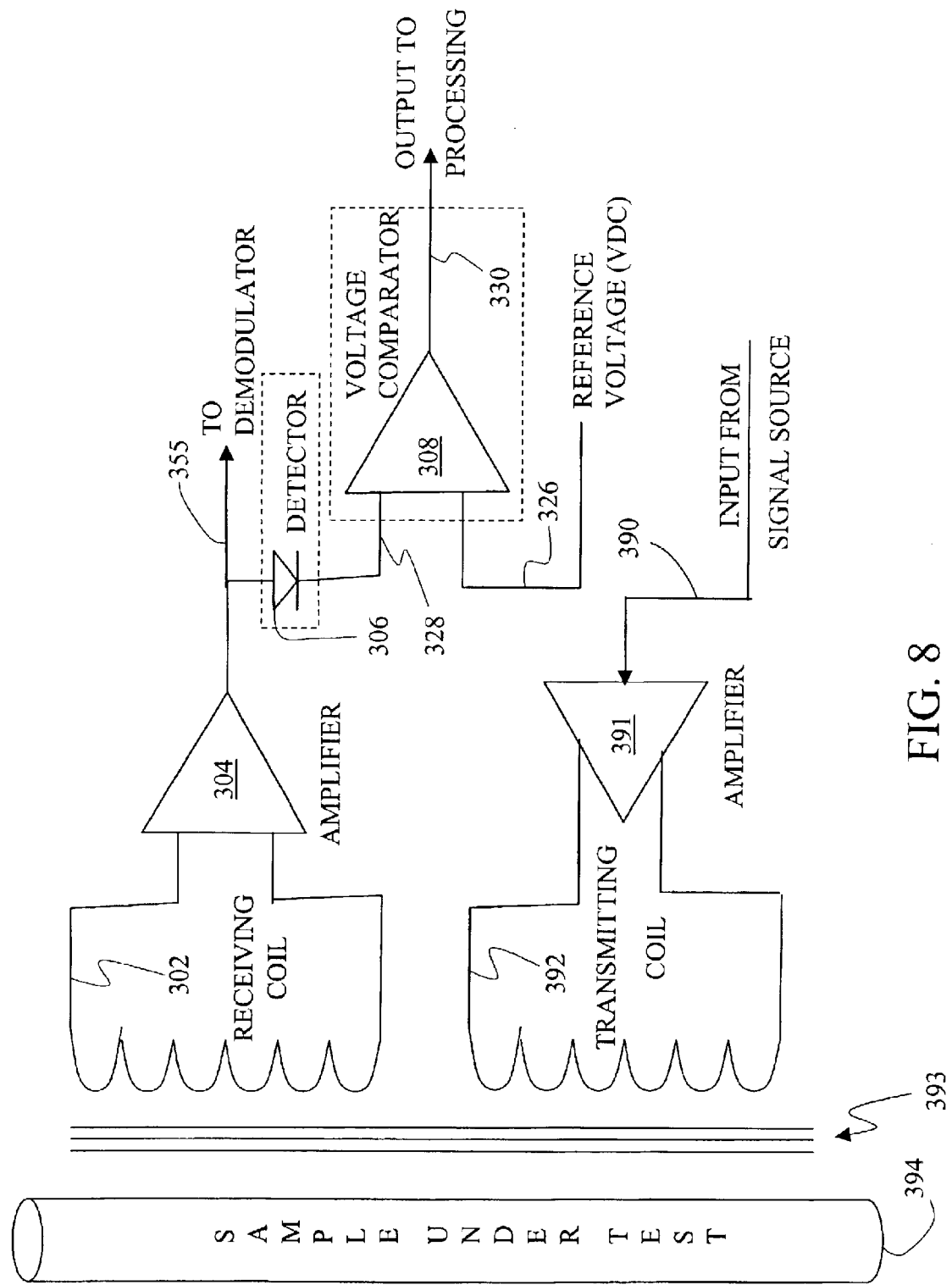
FIG. 8 illustrates an example sensing circuit by which the method of the present invention may be practiced.

FIG. 8 depicts one embodiment exploiting these phenomena. First, an input signal is sent to the transmitting coil amplifier 391. The transmitting coil 392 interacts with the specimen under test 394, where flux lines 393 are illustrated. The receiving coil 302 works as the front end of a sensor. The signal from the receiving coil 302 after passing through an amplifier stage 304 is coupled to a detector diode 306 and then to the input 328 of a voltage comparator 308. The reference voltage signal 326 combined with the detector output 328 to produce the processing system threshold trigger signal 330. A signal directly from the receiving amplifier stage 304 is sent to be demodulated 355.

Figure 9:
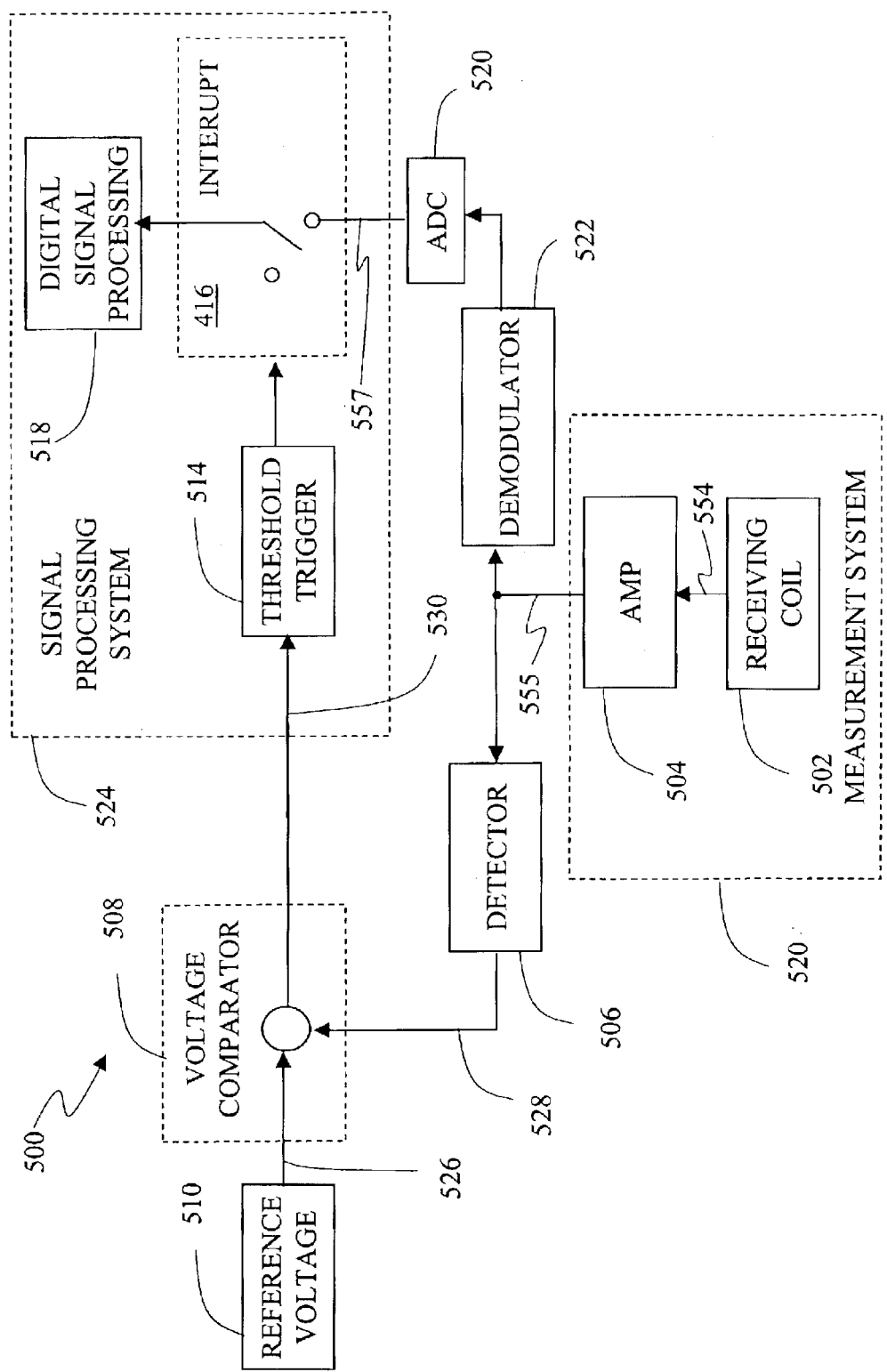
FIG. 9 is a block diagram illustrating an embodiment of the signal processing of present invention.

FIG. 9 illustrates in functional block diagram form that the measurement system 520 can be comprised of a receiving coil 502 and an amplifier 504, where the amp output 555 is sent to a detector 506 and a demodulator 522. The demodulated signal 556 (not shown) is passed to an analog-to-digital converter (ADC) 520. Absent interruption, the digital output of the ADC 557 is passed to the digital signal processing 518 of the signal processing system 524. The reference voltage 510 of the comparator can be set to a level that corresponds to the voltage generated on the coil when the sample is out of the transducer. Such an event will trigger an output change from this detector 528. The functional block diagram of FIG. 9 illustrates that the digital output 530 of this comparator 508 can then be used to trigger 514 an interrupt of the signal processing system 524 thus momentarily disabling 416 the measurement system 520 from sending control signals to the external equipment 518.

Figure 10:
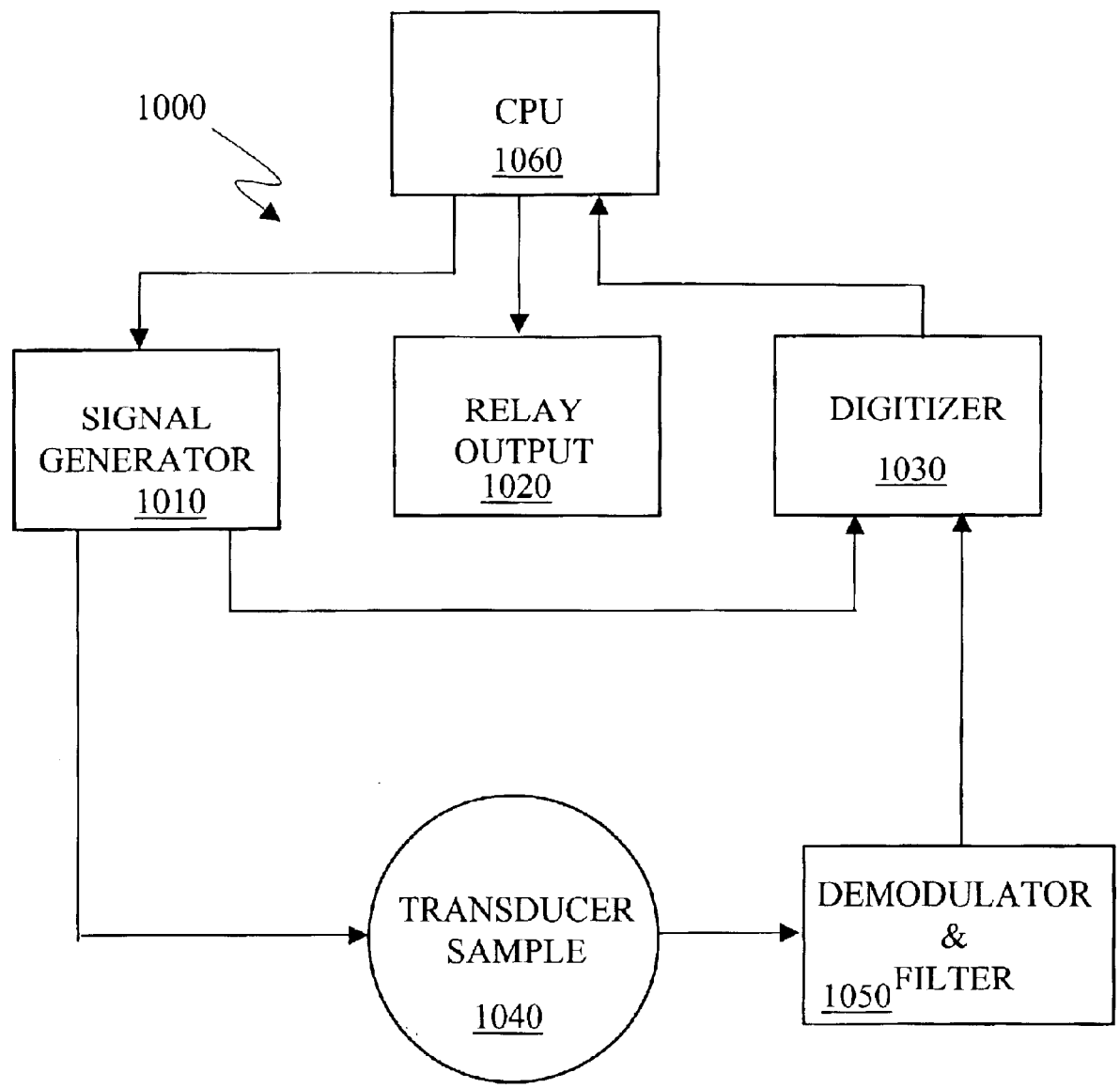
FIG. 10 is a functional block diagram of the present invention.

The signal processing loop 1000 of FIG. 10 consists of three principle means for signal processing and display. First a constant amplitude signal generation means 1010 with controllable sweep or dwell times. The programmable excitation time provides a greater signal to noise ratio allowing for the maximizing of measurement efficiency that is affected by varying material properties and alloy types. Additionally, the overall amplitude of the generated resonance is also a function of driving amplitude and the amplitude of the excitation signal is also controlled to maximize the received signal while keeping the receiver circuitry in a linear, non-saturated condition.

Another facet included in the system level embodiment exploited in order to further stabilize signal to noise performance is the use of a centering type of transducer-mount and material-handling fixture. This fixture maintains a stable center for the material during test minimizing electromagnetic coupling variations and thereby eliminating the wide voltage swings that would be presented to the receiver that would otherwise decrease the receiver's ability to demodulate the received signal. Further enhancing the economic advantage of using such a device is the stable center enables a given transducer to be utilized over a wider range of diameters since the receiver can be kept in its linear operating region.

Secondly there is a means of detection; the means for detection of the resonant signature of the material under test is accomplished by either of two techniques, analog or digital (DSP) demodulation. The analog demodulation method involves techniques similar to amplitude demodulation processes used in conventional radio frequency analysis while the digital demodulation methods can take the form of Fourier transforms or of LaPlace transforms and their respective inverses, for example. The demodulation process removes the RF information and passes the baseband phase and amplitude information through a filtering and amplification circuit. This demodulated information takes the shape of the time constant of the resonant event. The change in voltage and/or current in the one or more coils generates this electrical response detected by the receiver circuit as the material under test enters and passes through acoustic resonance. This signal change is a direct function of the changing transfer impedance between the one or more coils of the transducer and the kinds of samples under test.

The last element in the signal processing chain is the analog to digital conversion and subsequent signal processing performed by a computational means, in this case a microcomputer is used. The computational methods are of the form described previously. The entire system operates as a closed loop preferably under computer control. The digitized amplitude information is placed in an array and arranged such that an amplitude data point is mapped against its corresponding frequency point as this data is written into the array. While this is a sequential process the frequency sweep and corresponding captured data does not need to be lineal.

Figure 11:
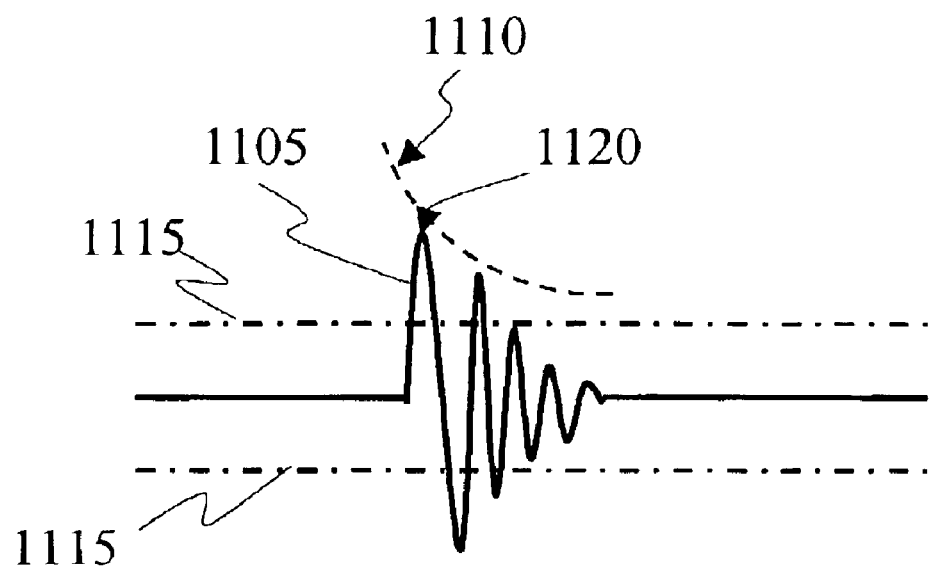
FIG. 11A illustrates the detected start of resonance at peak amplitude.
FIG. 11B illustrates the detected start of resonance at not at peak amplitude.
FIG. 11C illustrates the detected resonant frequency located at the center of tendency (amplitude)
FIG. 11D illustrates the detected resonant frequency located at the center of tendency (amplitude) for non-monotonically decaying envelope.
Figure 11:
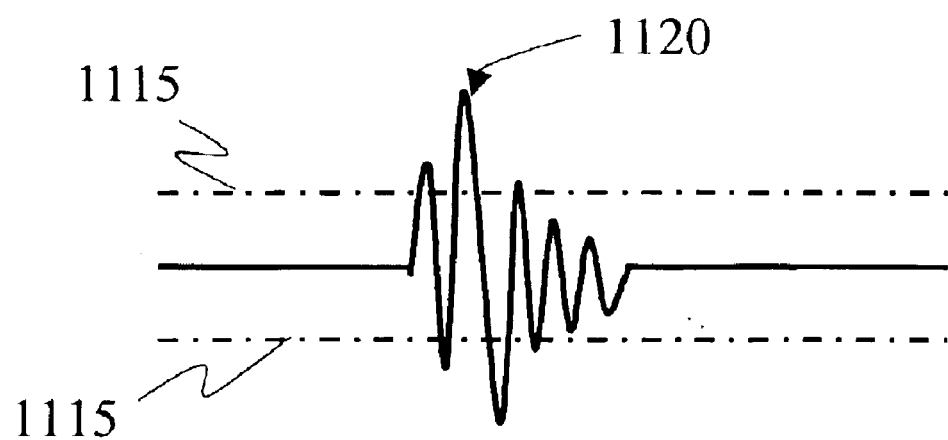
Figure 11:
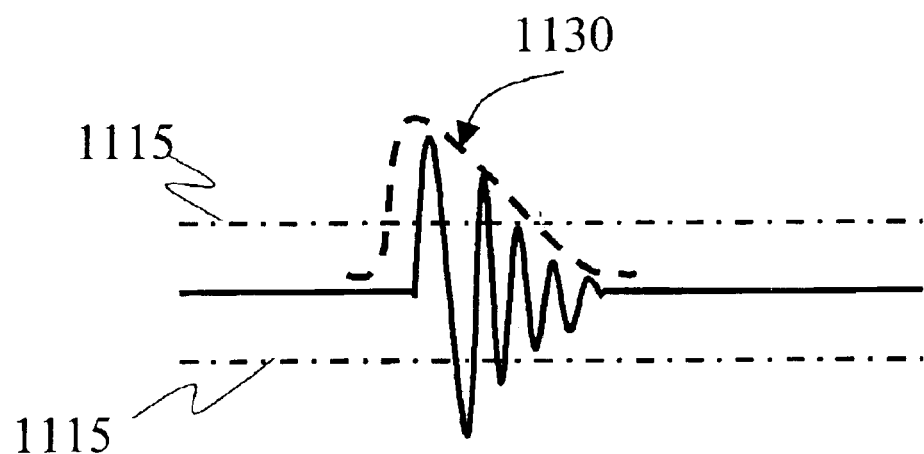
Figure 11:
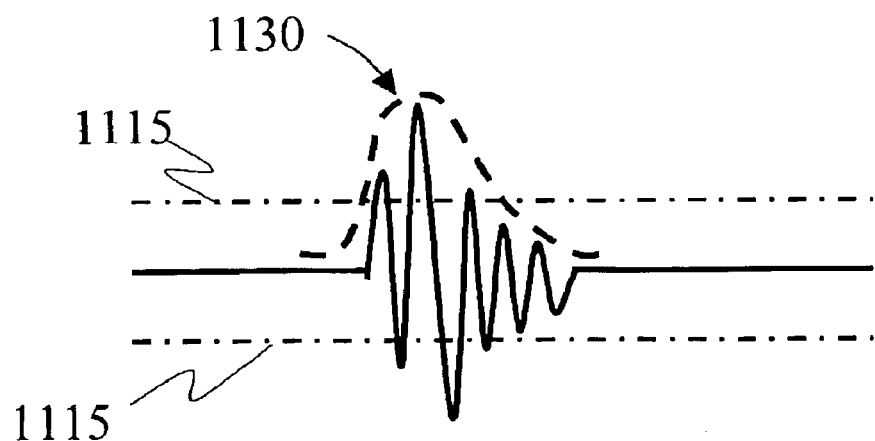

The digitized amplitude information contains the data from the entire sweep and if the frequency settings are proper the amplitude information of the acoustic resonance will be included. It is the position of this resonant event in primarily the frequency domain and secondarily the amplitude domain that determines the material properties of the sample under test. The position of the resonance in the sweep is determined by either of two means. Since the ideal shape of the resonant event 1105 has a form represented as a sinusoidal of exponentially decaying amplitude over time as shown in FIG. 11A, or more easily stated mathematically as an impulse function of the form $Ke^{-at}$ 1110. Simple peak detection using example detection thresholds 1115, whereby the peak amplitude point, $F_{peak}$ 1120 is extracted from an averaged, rectified waveform is often sufficient. Another more sophisticated numerical technique of interpolating the frequency of resonance by taking a weighted average, $F_{avg}$ 1130, of the peak power points of the resonance is also employed as shown in FIGS. 11C and 11D. The later is preferred since the variance in resonance caused by variance in normal material Qs does not necessarily place the peak amplitude at the same point as shown in FIG. 11B, although the net resonant frequency remains quite stable. Application of this type of computational technique minimizes the frequency jumping, possibly on the order of several kilohertz that would be indicated through the use of a simple peak detection technique. This means of providing a more stable center of tendency as shown in FIG. 11D leads to reduced anomaly detection sensitivity especially close in to the normal resonant signal envelope since the frequency deviation window must be enlarged to accommodate such frequency domain noise. An amplitude threshold as shown in FIGS. 11A–11D, provides a means by which an amplitude baseline is established acting as a filter for the purpose of minimizing noise or detecting loss of resonance is utilized in either previously taught numerical method. All signals above the reference are processed for resonance signals while amplitudes below reference are assigned a value of zero amplitude.

This threshold function becomes important since in the case of a defect where the volume exceeds a critical value in proportion to the volume under resonance the acoustic resonance will not display a trapped amplitude frequency shift but will actually lose significant Q and decay to zero or near zero amplitude. Rather than utilize time intensive numerical processes to extract the possible signal from any noise a simple axiomatic approach states that loss of overall quality and amplitude indicates poor material characteristics. Techniques taught in prior art detail a means to differentiate between the absence of material within the transducer or severe defect as being the cause of the loss of resonance.

Another method depending upon the inspection application is to generate the resonance just below the surface, in the case of a surface defect measurement application. Only if the defect volume interferes with this resonant field will the resonance be disturbed thus ignoring the effects of surface conditions that may be normal but present noise and signal processing problems that may affect material throughput capability.

Alterations and Modifications

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

I claim:

1. An apparatus for nondestructive testing of metallic structures comprising:
   (A) a housing having an opening surrounding an exterior wall of a metallic object having a longitudinal axis; said metallic object translatable, along its longitudinal axis, through the housing; and
   (B) a first electromagnetic acoustic transducer comprising:
      (1) a first plurality of substantially similar permanent magnets mounted in the housing and arranged in a first array and positioned substantially in planar radial fashion, about a first radial center, around the opening at substantially equal intervals with ends of adjacent magnets possessing opposite polarity; said first array positioned transverse to, and with the first radial center substantially colinear with, the longitudinal axis of said metallic object; each of said first plurality of substantially similar permanent magnets comprising:
         (a) a first end adjacent to the opening and
         (b) a second end substantially perpendicular to and spaced from the wall wherein the second end is notched in the plane substantially colinear with the longitudinal axis of the metallic object; and
      (2) a first electrically conductive wire coil mounted in the housing and positioned within an annular channel formed by the notched second ends of the first plurality of substantially similar permanent magnets.

2. The apparatus claimed in claim 1 wherein the opening is elliptical.

3. The apparatus claimed in claim 1 wherein the opening is substantially circular with a substantially flat sector.

4. The apparatus as claimed in claim 1 further comprising a second electromagnetic acoustic transducer comprising:
   (A) a second plurality of permanent magnets, substantially similar to the first plurality of substantially similar permanent magnets, mounted in the housing and arranged in a second array and positioned substantially in planar radial fashion, about a second radial center, around the opening at substantially equal intervals with ends of adjacent magnets possessing opposite polarity; the second array being substantially parallel and proximate to the first array; said second array plurality positioned transverse to and with the second radial center substantially colinear with, the longitudinal axis of the metallic object, each of said second plurality of magnets comprising:
      (1) a first end adjacent the opening and (2) a second end substantially perpendicular to and spaced from the wall wherein the second end is notched in the plane substantially colinear with the longitudinal axis of the metallic object; and
   (B) a second electrically conductive wire coil mounted in the housing and positioned within an annular channel formed by the notched second ends of the second plurality of permanent magnets.

5. The apparatus claimed in claim 4 wherein the opening is elliptical.

6. The apparatus claimed in claim 4 wherein the opening is substantially circular with a substantially flat sector.

7. The apparatus as claimed in claim 4 wherein the first array is rotationally offset in alignment relative to the second array.

8. The apparatus as claimed in claim 7 wherein spacing of each of the second end of the magnets is substantially consistent permitting the longitudinal travel of the metallic object without mechanically contacting the apparatus.

9. The apparatus as claimed in claim 8 wherein the first array and the second array are each comprised of twenty-six magnets.

10. An apparatus for nondestructive testing of metallic structures as claimed in claim 2 wherein the first electromagnetic acoustic transducer is separated from the second electromagnetic acoustic transducer by a dielectric spacer.

11. The apparatus as claimed in claim 4 further comprising
   (A) a signal generator coupled to the first electrically conductive wire coil;
   (B) a signal detector coupled to the second electrically conductive wire coil;
whereby the signal generator applies an electrical excitation signal to the first electrically conductive wire coil mounted in the channel of the first array, and the signal detector senses the electrical response signal in the second electrically conductive wire coil mounted in the channel of the second array.

12. The apparatus as claimed in claim 1 wherein an electrical excitation signal applied to the first electrically conductive wire coil induces vibrations in the metallic object.

13. The apparatus as claimed in claim 4 wherein acoustical vibrations in the metallic object electrically excite the second electrically conductive wire coil.

14. The apparatus as claimed in claim 4 wherein the first electromagnetic acoustic transducer is separated from the second electromagnetic acoustic transducer by a dielectric spacer.

15. An electromagnetic acoustic transducer comprising:

(A) a plurality of magnets mounted in a housing and arranged in an array and positioned substantially in a planar radial fashion, about a radial center, at substantially equal intervals around an opening of the housing with ends of adjacent magnets possessing opposite polarity; said opening providing a pass-through for a metallic object; said array positioned transverse to, and with the radial center substantially collinear with, a longitudinal axis of the metallic object, each of said plurality of magnets comprising:
  (1) a first end adjacent to the opening and
  (2) a second end substantially perpendicular to and spaced from an exterior longitudinal wall of the metallic object wherein the second end is notched in the plane substantially collinear with the longitudinal axis of the metallic object; and (B) an electrically conductive wire coil mounted in the housing and positioned within an annular channel formed by the notched second ends of the plurality of magnets.

\* \* \* \* \*